United States Patent
Uesugi et al.

[11] Patent Number: 5,129,268
[45] Date of Patent: Jul. 14, 1992

[54] METHOD OF MEASURING AVERAGE PARTICLE SIZE OF GRANULAR MATERIAL

[75] Inventors: Mitsuaki Uesugi; Masami Harayama, both of Kanagawa; Kazumi Ota, Toyama; Sotoaki Kawaguchi, Toyama; Hiroyuki Shibuya, Toyama, all of Japan

[73] Assignee: NKK Corporation, Tokyo, Japan

[21] Appl. No.: 496,335

[22] Filed: Mar. 20, 1990

[30] Foreign Application Priority Data

Apr. 5, 1989 [JP] Japan ................................ 1-84874

[51] Int. Cl.$^5$ ........................................... G01N 15/02
[52] U.S. Cl. .................................. 73/865.5; 356/335; 364/555; 382/1
[58] Field of Search ................ 73/865.5, 866, 865.8; 356/335, 336; 364/555; 382/1, 8; 377/11

[56] References Cited

U.S. PATENT DOCUMENTS

| | | | |
|---|---|---|---|
| 3,377,597 | 4/1968 | Muta | 73/865.5 X |
| 3,782,827 | 1/1974 | Nisenson et al. | 356/376 |
| 4,233,664 | 11/1980 | Grandchamp | 356/336 X |
| 4,239,612 | 12/1980 | Goetz | 204/299 R |
| 4,259,015 | 3/1981 | Wada | 356/336 |
| 4,463,600 | 8/1984 | Hobbs et al. | 73/81 |
| 4,781,460 | 11/1988 | Bott | 356/338 X |

FOREIGN PATENT DOCUMENTS

| | | | |
|---|---|---|---|
| 148558 | 11/1979 | Japan . | |
| 90139 | 6/1982 | Japan | 73/865.5 |
| 190248 | 11/1982 | Japan | 73/865.5 |
| 187135 | 8/1988 | Japan | 73/865.5 |
| 279142 | 11/1988 | Japan | 73/865.5 |
| 2012948 | 8/1979 | United Kingdom | 73/865.5 |

*Primary Examiner*—Tom Noland
*Attorney, Agent, or Firm*—Michael N. Meller

[57] ABSTRACT

A method of measuring an average particle size of granules. The method computes the average particle size on the basis of an n-order moment $M_n$ of an image of granules accumulated in a pile or of the image subjected to binarization or floating binarization. The method is capable of highly accurate and stable measurement on granules having many irregularities in the surface thereof and accumulated in a pile. The method can be used to continuously measure in real time the particle size of granules in a rotary tray of a rotary tray-type rolling granulating machine thereby adjusting the feed rate of a liquid binder to automatically control the particle size.

13 Claims, 10 Drawing Sheets

FIG. 1a

REFERENCE IMAGE $f(x,y)$
(PARTICLE SIZE = 1)

FIG. 1b

MEASURED IMAGE $f(\frac{x}{a}, \frac{y}{a})$
(PARTICLE SIZE = a)

FIG. 1c

| ORIGINAL IMAGE | POWER SPECTRUM | n-ORDER MOMENT OF SPECTRUM |
|---|---|---|
| $f(x,y)$ | $\overline{P}(u,v) = |F(u,v)|^2$ | $\overline{M}_n = \int_0^\infty u^n \overline{P}(u,0) du$ |
| $f(\frac{x}{a}, \frac{y}{a})$ | $a^4 \overline{P}(au, av)$ | $M_n = a^{3-n} \overline{M}_n$ |

FIG. 2a ORIGINAL IMAGE

FIG. 2b BLURRED IMAGE

FIG. 2c PARTICLE SIZE EXTRACTING IMAGE

FIG. 2d
POWER SPECTRUM

AVERAGE PARTICLE SIZE $\tilde{a} = B\sqrt{M_0/M_2}$ ---(1)
$M_0$ : POWER SPECTRUM 0-ORDER MOMENT
$M_2$ : POWER SPECTRUM SECOND-ORDER MOMENT (REFERENCE) $M_k = \int_0^\infty u^k P(u) du$ POWER SPECTRUM P(u)
u : SPATIAL FREQUENCY

| ORE GRADE | PERCENTAGE | WATER CONTENT |
|---|---|---|
| SOUTH AFRICA BF | 40.0 | 4.5 |
| IRAN | 27.5 | 7.6 |
| OMC-HF | 30.0 | 13.7 |
| BENTONITE | 2.5 | 8.0 |

| | |
|---|---|
| ORE FEED RATE | 16 T/Hr |
| DESIRED PARTICLE SIZE | 12.0 mm |
| LIQUID BINDER FEED (WATER) | 7.7~8.4 ℓ/min |
| PARTICLE SIZE STANDARD DEVIATION | $\sigma = 0.34$ |
| MAXIMUM PARTICLE SIZE | 12.6 (mm) |
| MINIMUM PARTICLE SIZE | 11.3 (mm) |

| IMAGE PICKUP CONDITIONS | SHUTTER SPEED | 1/4000 (S) |
| | APERTURE | F-4.2 |
| | DISTANCE | 1500 mm |

FIG. 7

| ORE GRADE | PERCENTAGE | WATER CONTENT |
|---|---|---|
| SOUTH AFRICA BF | 40.0 | 4.7 |
| IRAN | 27.5 | 7.5 |
| OMC-HF | 30.0 | 13.5 |
| BENTONITE | 2.5 | 8.0 |
| ORE FEED RATE | | 15 T/Hr |
| DESIRED PARTICLE SIZE | | 12.0 mm |
| LIQUID BINDER FEED (WATER) | | 7.5~9.6 ℓ/min |
| PARTICLE SIZE STANDARD DEVIATION | | $\sigma = 1.32$ |
| MAXIMUM PARTICLE SIZE | | 15.7 (mm) |
| MINIMUM PARTICLE SIZE | | 8.7 (mm) |
| IMAGE PICKUP CONDITIONS | SHUTTER SPEED | 1/4000 (S) |
| | APERTURE | F-4.2 |
| | DISTANCE | 1500 mm |

METHOD OF MEASURING AVERAGE PARTICLE SIZE OF GRANULAR MATERIAL

BACKGROUND OF THE INVENTION

The present invention relates to a measuring method for continuously measuring, in a non-contact manner, the average particle size of granular material accumulated in a pile by use of image processing.

In the case of a blast furnace or electric furnace, it has been known that there exists a high degree of correlation between the average particle sizes of its raw materials, e.g., sintered ore, cokes and pellets and the furnace operating conditions and the particle size control of these charges has been an essential point for the stable operation of the furnace. In the past, however, there has been no suitable method capable of measuring such particle sizes in a short period of time and in a simple way and therefore the control has been effected by relying on the visual observations of the operator or the sampling measurement of the order of several times a day, thus failing to ensure satisfactory control accuracy.

On the other hand, if the average particle size of such charges can be continuously measured, for example, on a conveyor or on a granulating machine or pelletizer in the case of pellets, the particle size control of the charges can be improved rapidly with the resulting great contribution toward the stable operation of the furnace. From this point of view heretofore much has been expected of the development of a system for measuring the average particle size of granular material accumulated in a pile in a continuous and non-contact manner.

To meet this demand, as disclosed for example in Japanese Laid-Open Patent No. 54-148558, there has been proposed in the past a method of determining the average particle size of granular material accumulated in a pile by televising the granular material with a television camera and processing the resulting image.

In the method disclosed in Japanese Laid-Open Patent No. 54-148558, the charged material being transported by a belt conveyor is illuminated by a flashlight and picked up with a television camera, thereby enhancing the contrast of the image by a video processing equipment. Thereafter, the image enhanced in contrast is applied through a processed image generator to a picture roughness measuring unit which in turn determines the repetition frequency of the light and shade greater in contrast than a given level (corresponding to the average intergranule distance) with respect to the selected scanning lines, and then the light and shade repetition frequency is converted to the average particle size by a computing unit, thereby displaying it on a display unit.

The method disclosed in Japanese Laid-Open Patent No. 54-148558 is a method in which the so-called average inter-granule distance of the granular material shown in the picture is determined to estimate the average particle size. Thus, where the materials to be measured are, for example, the raw materials for steel which are each accumulated in a pile, variations tend to be caused in the measurements and it is difficult to ensure satisfactory measuring accuracy due to the following factors:

1) In the case of sintered ore, coke or pellets under granulation, there are many irregularities in the surface of the granules and they tend to cause the shading which tends to be mistaken for granule-granule boundaries.

2) When accumulated in a pile, the granule-granule boundaries are not clear in many cases and adjacent two granules tend to be mistaken for a single granule.

As described hereinabove, the method of processing the image itself to measure the period of light and shade has tended to suffer the effect of disturbances.

SUMMARY OF THE INVENTION

It is an object of the present invention to provide a method of measuring the average particle size of granules by computing the power spectrum of an image by spatial frequency analysis and processing the power spectrum to determine a quantity corresponding to the frequency of light and shade, thereby spreading disturbance noise over all frequencies on the spectrum and reducing the effect of the disturbances.

The present invention notes the fact that in the image resulting from picking up of granules accumulated in a pile. Considering the power spectrum of the image, there is a tendency that the spectrum spreads (the high frequency components increase) with decrease in the average particle size and that the spectrum reduces (the low frequency components increase) with increase in the average particle size, and the spreading of the spectrum is evaluated by the n-order moment, thereby measuring the average particle size.

In accordance with the present invention, the average particle size of granules is determined by using the moment of at least one order to the n-order moment $M_n(n=0,1,2...)$ of the picked up image of the granules accumulated in a pile. Thus, by virtue of the fact that the average particle size is determined in accordance with n-order moment $M_n$ of the power spectrum of the image of the granules accumulated in a pile, it is possible to make a highly accurate and stable measurement on granules having many irregularities in the surface and accumulated in a pile.

Further, in accordance with the present invention the average particle size of granules accumulated in a pile is determined by using the n-order moment $M_n(n=0, 1, 2, ...)$ of the power spectrum of a granule extracting image obtained by the binarization or floating binarization of the picked up image of the granules. By thus using the image subjected to the binarization or the floating binarization, not only the variations in the brightness of the image are removed but also the contours of the granules are further emphasized, thereby ensuring measurements with a high degree of accuracy.

Still further, in accordance with the present invention, in determining the average particle size $\tilde{a}$ of the granules from the n-order moment $M_n$ ($n=0, 1, 2, ...$) of the power spectrum of the image, the value of $\tilde{a}$ is determined from the following computational expression by using two moments $M_l$ and $M_{l+k}$ ($l=0, 1, 2, ..., k=1, 2, 3, ...$) of different orders from each other.

$$\tilde{a} = B \cdot \sqrt[k]{M_l/M_{l+k}} \quad (B: \text{proportionality factor})$$

By thus computing to determine the average particle size $\tilde{a}$, it is possible to make the measurement which is not affected by variations in the brightness of the image due to such disturbances as variation in the illuminating light quantity and the granule surface reflectance.

Still further, in accordance with the present invention, when determining the n-order moment of the power spectrum, the image is horizontally or vertically divided into $\underline{m}$ parts so that the image signal is vertically and horizontally averaged within each divided part and the power spectrum of the signal is determined. Then, the thus determined $\underline{m}$ power spectra are averaged and the resulting average power spectrum P(u) is used to determine an n-order moment $M_n$ from the following expression $$M_n = \int_0^\infty u^n P(u) du$$

In this way, in the computation of the power spectrum of the image, these $\underline{m}$ power spectra are averaged and the resulting average power spectrum P(u) is used to compute the moment of the power spectrum, thereby reducing the computing time.

Stil further, in accordance with the present invention, the average particle size of granules in the tray of a rotary tray-type granulating machine is measured with a high degree of accuracy by the above-mentioned measuring method to adjust the feed rate of a liquid binder, thereby producing uniform granulated material.

BRIEF DESCRIPTION OF THE DRAWINGS

These figures are collectively referred to FIG. 2.

DESCRIPTION OF THE PREFERRED EMBODIMENTS

Prior to the description of its preferred embodiment, the principle of the present invention will be described first.

Figure 1A:
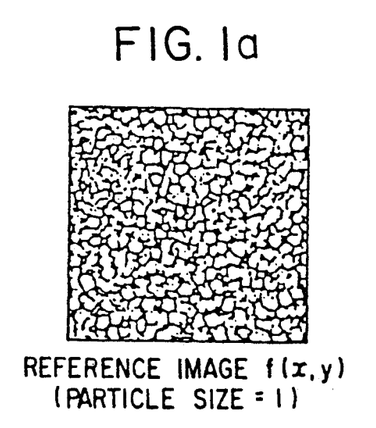
FIG. 1a, 1b and 1c show expressions for the computation of the power spectrum of a granule image and the n-order moment of the power spectrum according to the present invention. These figures are collectively referred to FIG. 1.
Figure 1B:
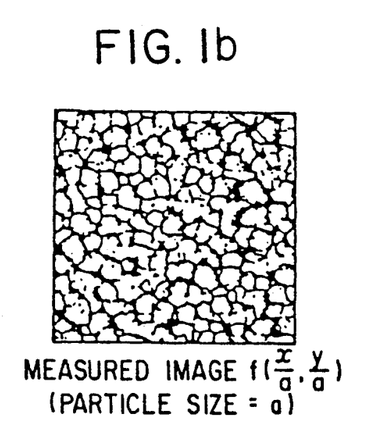
Figure 1C:
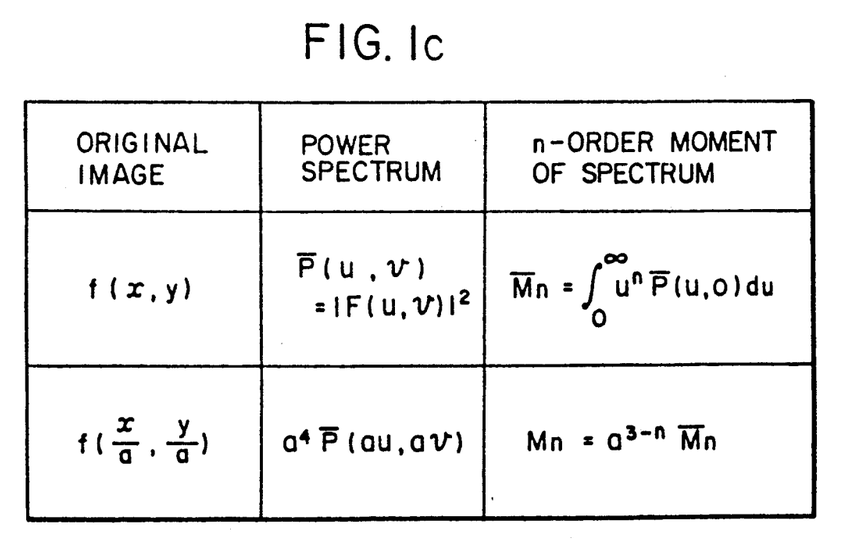

FIG. 1 shows expressions for computing the n-order moment of the power spectrum of a granule image. In the Figure, it is assumed that (a) shows a particle size reference image f(x, y) and (b) shows the image f(x, y) enlarged $\underline{a}$ times in the x-direction and the y-direction, i.e., an image increased $\underline{a}$ times in particle size over the particle size reference image. At this time, the image of (b) is given as follows:

$$f\left(\frac{x}{a}, \frac{y}{a}\right)$$

The power spectra of the two images can be determined as shown by the following expressions.

1) Power spectrum $\overline{P}(u, v)$ of reference image $$\overline{P}(u, v) = |\overline{F}(u, v)|^2 \quad (1)$$

$$= \left| \int_{-\infty}^{\infty} \int_{-\infty}^{\infty} f(x, y) e^{-2\pi j(ux+vy)} dx dy \right|^2$$

2) Power spectrum P(u, v) of enlarged image $$P(u, v) = |F(u, v)|^2 \quad (2)$$

$$= \left| \int_{-\infty}^{\infty} \int_{-\infty}^{\infty} f\left(\frac{x}{a}, \frac{y}{a}\right) e^{-2\pi j(ux+vy)} dx dy \right|^2$$

$$= \left| a^2 \int_{-\infty}^{\infty} \int_{-\infty}^{\infty} f(x, y) e^{-2\pi j(aux+avy)} dx dy \right|^2$$

$$= a^4 \overline{P}(au, av) \quad (u, v: \text{spatial frequencies})$$

Thus, the power spectrum P(u,v) of the $\underline{a}$-fold enlarged image takes the form of a spectrum which is reduced by 1/a in each of the spatial frequency $\underline{u}$ and $\underline{v}$ directions as compared with the power spectrum $\overline{P}(u,v)$ of the reference image.

Then, in order to evaluate the spreads of the spectrum, let us obtain the n-order moments of the power spectral. In this case, assuming for purposes of simplicity that the spectrum has an axially symmetric form with respect to the origin, the moments of the spatial frequency $\underline{u}$ direction spectrum $\overline{P}(u,o)$ and P(u,o) are calculated.

1) The n-order moment $\overline{M}_n$ of the power spectrum of reference image $$\overline{M}_n = \int_0^\infty u^n \overline{P}(u, o) du \quad (3)$$

2) The n-order moment $M_n$ of the power spectrum of enlarged image $$M_n = \int_0^\infty u^n P(u, o) du \quad (3)$$

$$= \int_0^\infty u^n a^4 \overline{P}(au, o) du$$

$$= a^4 \int_0^\infty a^{-(n+1)} u^n \overline{P}(u, o) du$$

$$= a^{3-n} \overline{M}_n \quad (4)$$

It will be seen that the estimated value $\tilde{a}$ of the average particle size is given as follows from equation (4)

$$\tilde{a} = A M_n^{\frac{1}{3-n}} \quad (5)$$

where $$A = M_n^{-\frac{1}{3-n}}$$

(proportional constant)

Therefore, the average particle size of granules accumulated in a pile can be determined by using the n-order moment of the power spectrum of a granule image.

Next, considering, for example, variations in the brightness of a granule image due to variations in the average particle size, such disturbances in variations in the illuminance of the illumination and variations in the reflectance of an object to be measured, let us conceive to make the evaluation by using the ratio between two moments, $M_l$ and $M_{l+k}$, of the different orders so as to ensure only the sensitivity to variations in the average particle size without being affected by these disturbances. From equation (4) we obtain $$M_l/M_{l+k} = a^k \overline{M}_l/\overline{M}_{l+k} \qquad (6)$$

Therefore, the estimated value $\tilde{a}$ of the average particle size is given by the following:

$$a = B \cdot \sqrt[k]{M_l/M_{l+k}} \qquad (7)$$

$(l = 0, 1, 2, \ldots, k = 1, 2, 3 \ldots)$ where $B = (\overline{M}_{l+k}/\overline{M}_l)^{1/k}$ (proportional constant)

As described hereinabove, it has been found out that the average particle size can be determined by using the moment of at least one order of the n-order moment of the power spectrum of a granule image.

FIG. 2 shows an example of the computing sequence of an average particle size $\tilde{a}$ in accordance with the above-mentioned method.

Where there are variations in the brightness of the original image in (a) of FIG. 2 due for example to variations in the illumination, the illumination variations are previously removed by subtracting from the original image the blurred image of (b) which has been obtained from the original image by the moving average method. While the following power spectrum computation may be directly performed on the basis of this image, in the case of FIG. 2. in order to further enhance the contours, the image is binarized to preliminarily compute a granule extracting image (to subtract the blurred image from the original image and binarize the resultant image corresponds to subjecting the original image to floating binarization).

Then, while the computation of a spectrum from the granule image may be effected by the two-dimensional Fourier transform in order to simplify the computation and redo the computing time, in FIG. 2 the granule extracting image is horizontally divided into $\underline{m}$ parts so that in each of the divided parts the image signal is vertically averaged and the one dimensional power spectrum of the resulting signal is determined. The thus determined $\underline{m}$ power spectra are averaged and the resulting power spectrum P(u) is used as the P(u,o) in equation (4).

Figure 2A:
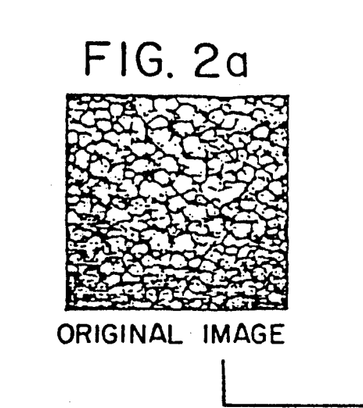
FIG. 2a, 2b, 2c and 2d show an example of an average particle size computing sequence according to the present invention.
Figure 2B:
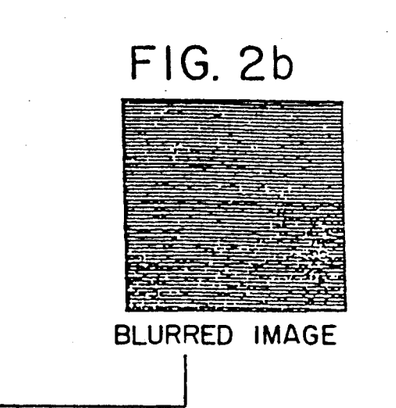
Figure 2C:
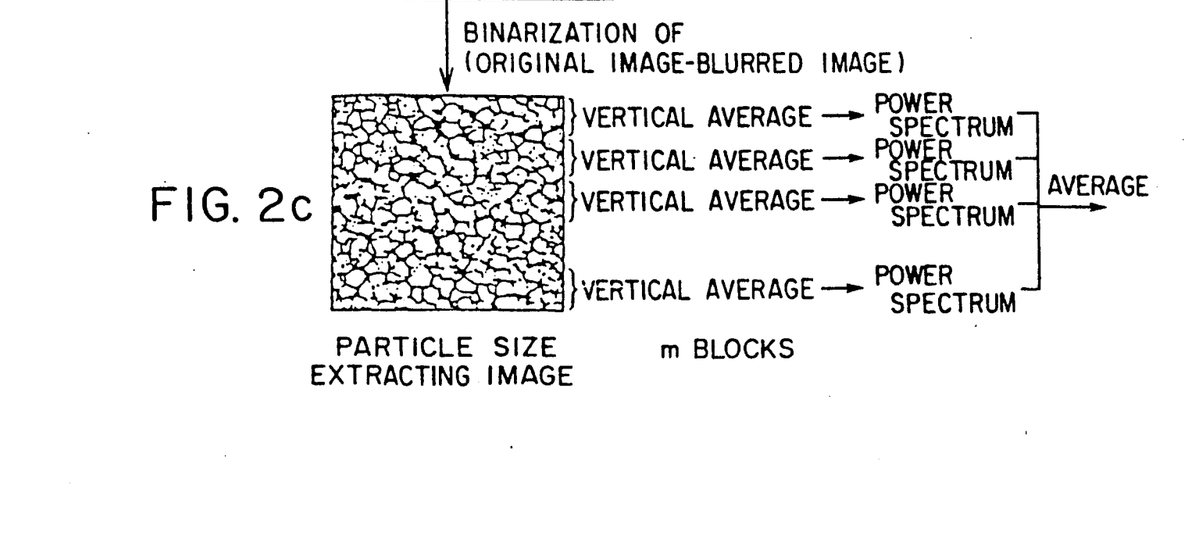

It is to be noted that the direction of the division may be the vertical direction instead of the horizontal direction and the direction of averaging of the image signal may be the horizontal direction instead of the vertical direction.

Figure 2D:
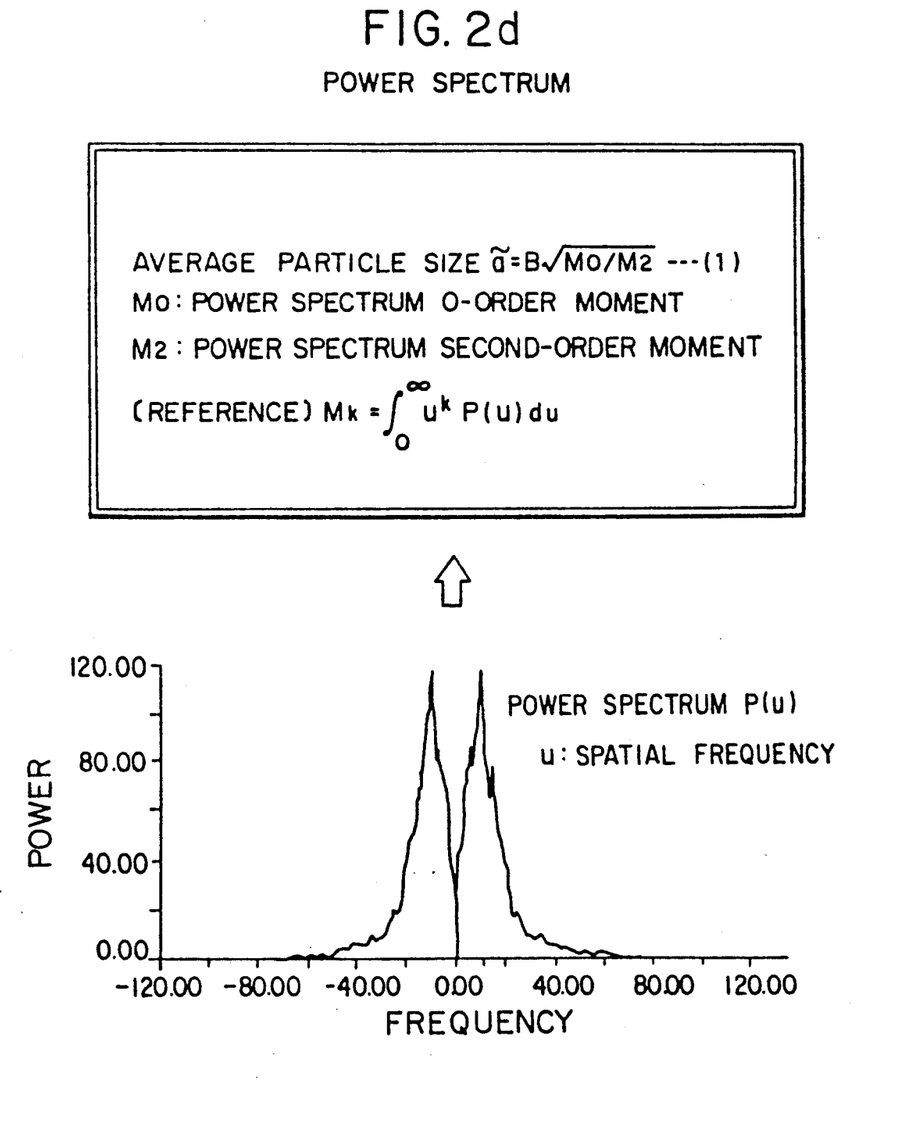

Then, as the l-order and (l+k)-order moments of the power spectrum, the 0-order moment $M_o$ and the second-order moment $M_2$ are for example obtained from equation (4) and the average particle size $\tilde{a}$ is computed in accordance with equation (7).

In this case, it is assumed that the proportional constant B is preliminarily determined by measuring with the same method any material to be measured whose particle size is already known.

Figure 3:
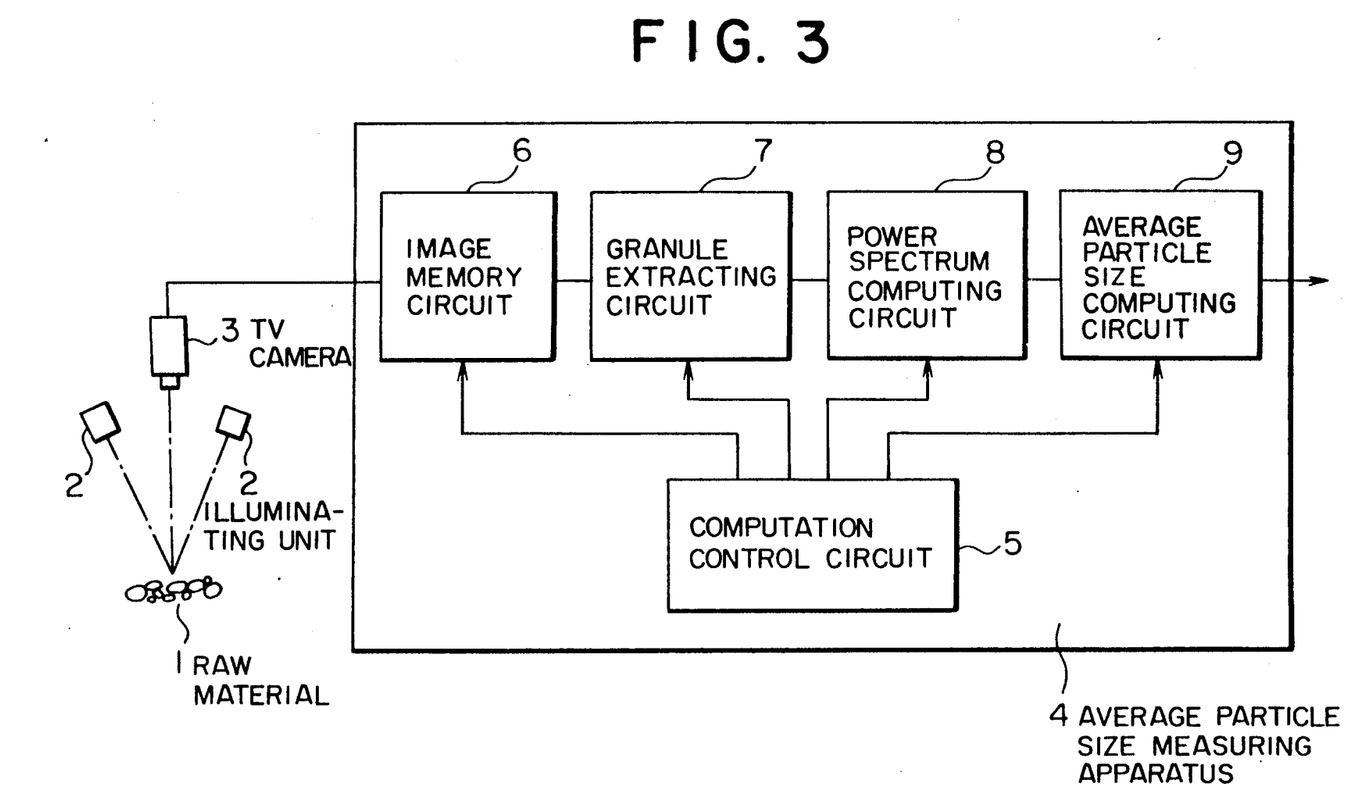
FIG. 3 is a block diagram showing an apparatus for measuring the average particle size of granules according to an embodiment of the present invention.

Referring now to FIG. 3, there is illustrated a block diagram of a granule average particle size measuring apparatus for performing the method according to the embodiment of the present invention. Raw material 1 transported by for example a belt conveyor is illuminated by one or more illuminating units 2 which are arranged obliquely above the raw material so as to facilitate the discrimination of the granule-granule boundaries and the resulting reflected light image is picked up from above by a television camera 3. At this time, in order to prevent the image from being blurred due to the movement of the raw material 1, a stroboscopic illumination is used for each illumination, unit 2 or alternatively a camera with a high-speed shutter is used as the television camera 3.

The image picked up by the television camera 3 is applied as an electric signal to an average particle size measuring apparatus 4. The average particle size measuring apparatus 4 incorporates a computation control, circuit 5 and the computation of an average particle size is entirely performed sequentially in response to computation synchronizing signals generated from the computation control circuit 5.

The applied image signal is divided for example into meshes with 256 points × 240 points crosswise in an image memory circuit 6 and the brightness at the respective points are digitized in 256 gradations, thereby storing the image signal for one frame. The stored image is sent to the following granule extracting circuit 7 in response to the command from the computation control circuit 5. In the granule extracting circuit 7, the input image is subjected to the floating binarization as shown in FIG. 2 so that a granule extracting image is obtained and stored therein. The granule extracting image is sent to the following power spectrum computing circuit 8.

The power spectrum computing circuit 8 horizontally divides the granule extracting image into $\underline{m}$ parts as shown in FIG. 2, so that in each of the divided parts the image signal is vertically averaged and the power spectrum of the resulting signal is determined. The average power spectrum P(u) of the thus determined $\underline{m}$ power spectrum is computed and outputted. This average power spectrum P(u) is transferred to an average particle size computing circuit 9. The average particle size computing circuit 9 computes two moments of the different orders from the average power spectrum P(u) so that the average particle size a is computed from these moments and outputted.

Next, a description will be given of a method in which the above-described granule average particle size measuring method is applied to an automatic control of a rotary tray-type rolling granulating machine to produce uniform granulated material.

Prior to this explanation, the background art of the granulating techniques for granulated material will be first described.

The granulating techniques for granulated material are broadly classified into two types, i.e., self-contained granulation and forced granulation. The former includes granulating mechanisms based on the use of rolling, fluidized bed, agitation, etc., and they are used in applications where the deformation of granule shape is relatively tolerated and mass treatment is used. The latter includes granulating mechanisms based on the use of extrusion, compression, etc., and they are used for the production of granules which are uniform in granule shape and are compact.

Where relatively large granules (10-15 mm) are mass produced as in the case of treating ore raw materials, the self-contained granulation, particularly the rolling granulation method is mainly used. This rolling granulation method is such that a liquid binder is spread onto the feed powder material in an inclined rotary tray to form agglomerated granulated material and the classifying effect of the rotary is utilized to grow the granulated material to the desired particle size, thereby discharging the products from a rim.

With this method, since the particle size tends to vary due, for example, to variations in the moisture content of the feed powder materials and the granule shape, it has been necessary for the operator to adjust the amount of the liquid binder, etc., depending on the circumstances while always monitoring by visual inspection. In this case, it has been difficult for the monitoring with the naked eye to accurately grasp the particle sizes of granulated material moving at a high velocity, thus failing to ensure a satisfactory particle size control accuracy and thereby causing variations of ±15 to 10 mm in terms of the visual range.

This rolling granulation method is high in production cost due to the fact that a preliminary treatment such as drying or sizing the feed powder material is required for the stabilization of the granulation process and that the operator must always be posted. Also, due to the monitoring with the naked eye and the manual control, the particle size control cannot be effected with satisfactory accuracy and it is a major cause for impeding the stabilization of the following process. In view of these circumstances, there has been a long felt need for the establishment of the method of measuring the average particle size of granules according to the present invention.

The background of the granulation techniques has been clarified so far and a description will now be made of the method of automatically controlling the particle size of granulated material by a rotary tray-type rolling granulating machine to which the present invention is applied.

Figure 4:
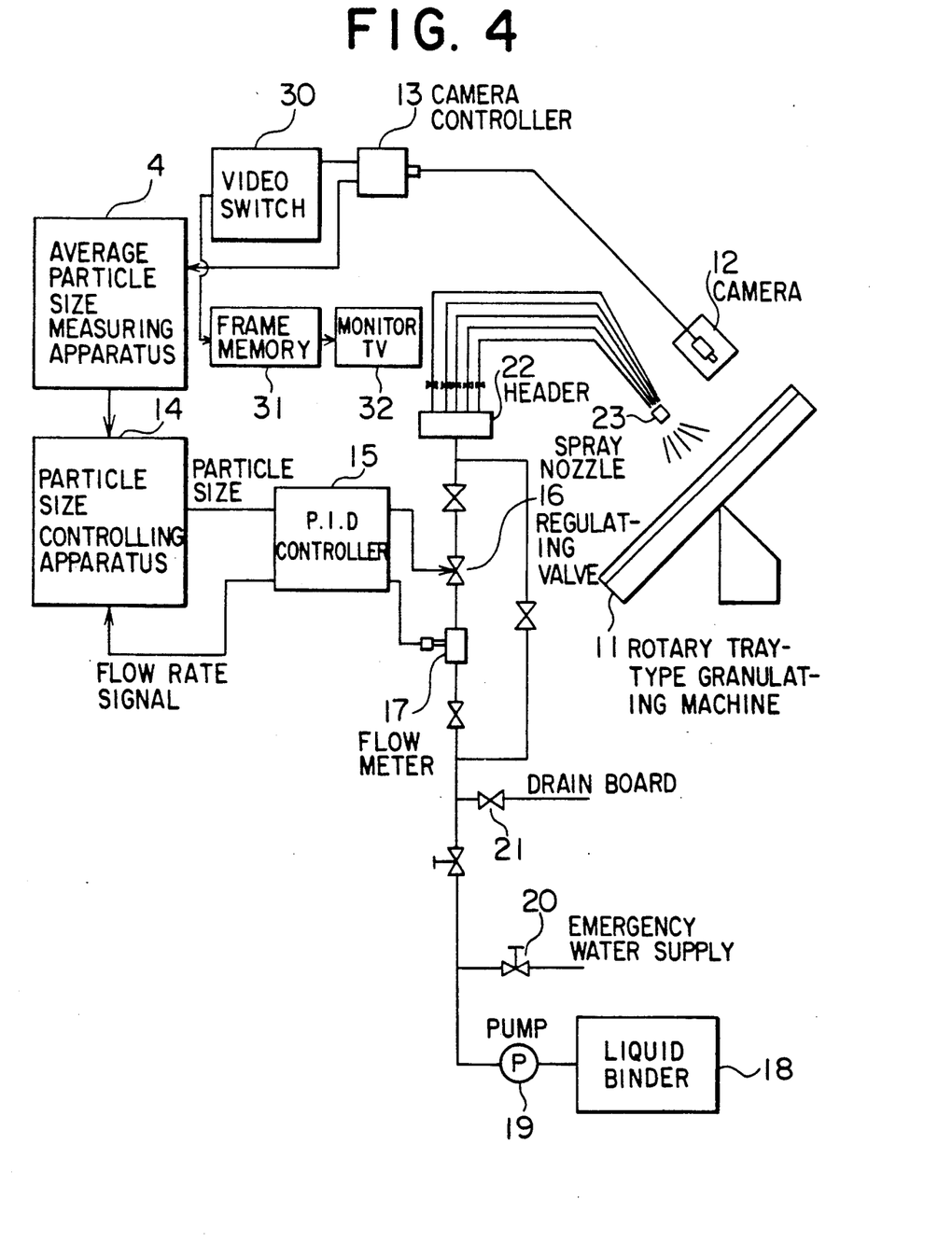
FIG. 4 is a schematic block diagram useful for explaining a particle size automatic controlling apparatus for granulated material and its associated equipment according to another embodiment of the present invention.

Referring to FIG. 4, there is illustrated a schematic block diagram showing a granule particle size automatic control apparatus and its related equipment. In the Figure, numeral 11 designates a rotary tray-type rolling granulating apparatus which performs a granulating process on a variety of powder materials to be treated which are not subjected to such preliminary treatments as drying and sizing and which are different in moisture content and granular properties. Numeral 12 designates a CCD high-speed camera for picking up an image of the granules in the rotary tray of the rotary tray-type rolling granulating machine 11. Numeral 13 designates a camera controller which sends the granule image picked up by the CCD high-speed camera 12 to the average particle size measuring apparatus 4 described in connection with FIG. 3, thereby sequentially measuring the particle size in real time.

Numeral 14 designal a particle size controlling apparatus for computing the flow rate of the liquid binder in accordance with the particle size from the average particle size measuring apparatus 4 numeral 15 designates a PID controller, and 16 a control valve. These devices control the flow rate of the liquid binder in accordance with the result of the computation made in the particle size controlling apparatus 14. Numeral 17 designates an electro magnetic flow meter for measuring the flow rate of the liquid binder and feeding it back to the PID controller 15.

Numeral 18 designates a liquid binder tank, and 19 a pump for forcing out the liquid binder from the tank, 18. Numeral 20 designates a valve for supplying emergency feed water, and 21 a valve for discharging the drain. Numeral 22 designates a header, and 23 a spray nozzle.

Numeral 30 designates a video switch, 31 a frame memory and 32 a monitor television. These means monitor the granule image picked up by the CCD high-speed camera 12.

With the apparatus constructed as described above, an image of the granules in the rotary tray of the rotary-tray type rolling granulating machine 11 is picked up by the CCD high-speed camera 12 and the image is sent through the camera controller 13 to the average particle size measuring apparatus 4 which in turn measures the particle size by the method described in detail in connection with FIG. 3. Then, in accordance with the particle size from the average particle size measuring apparatus 4, the flow rate of the liquid binder is computed so that the opening of the control valve 16 is adjusted by the PID controller 15 and the flow rate of the liquid binder from the liquid binder tank 18 is adjusted. Then, the liquid binder is delivered to the spray nozzle 23 through the header 22 and the liquid binder is sprayed onto the granules in the rotary tray of the rotary tray-type rolling granulating machine 11 from the spray nozzle 23, thereby producing the granulated material of the desired particle size.

EXAMPLE 1

Figure 5:
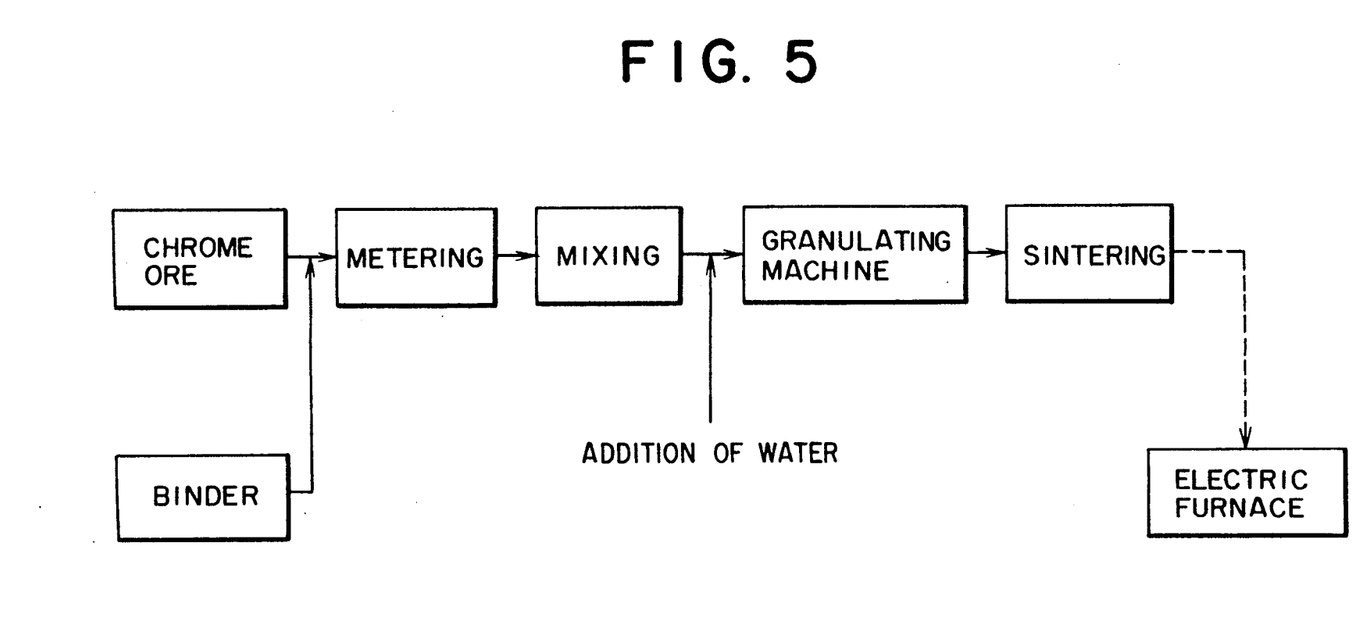
FIG. 5 is a flow diagram showing the manufacturing process of chromium ore pellets.

The production of chromium ore pellets was performed by the manufacturing process shown in FIG. 5. 300 Tons of chromium ore fines in outdoor storage were loaded into a stock bin without being subjected to such preliminary treatments as drying and sizing and then delivered in constant amounts at the rate of 15 T/Hr. 2.5% of bentonite as the binder was added and mixed with the material in a ball mill and the mixture was subjected to rolling granulation in the rotary tray.

In this case, the adjustment of the liquid binder (water) quantity was effected by using the apparatus shown in FIG. 4. The image picked up by the television camera 12 is applied as an electric signal to the average particle size measuring apparatus 4 where the particle size was computed at intervals of 6 seconds and they were averaged over 60 seconds (the particle sizes for 10 points), thereby sending the resulting output value to the particle size controlling apparatus 14. At this time, the flow rate data was received from the electromagnetic flow meter 17 to issue a flow rate adjusting command so that the water quantity was decreased when the particle size was greater and the water quantity was increased when the particle size was smaller, and the opening of the control valve 16 was adjusted by the PID controller 15 in accordance with a preset sensitivity. At this time, the PID set values were such that P (proportional band) was 350%, I(integral time 250 seconds and derivative time) 180 seconds. The results are shown in FIGS. 6 and 8.

Figure 6:
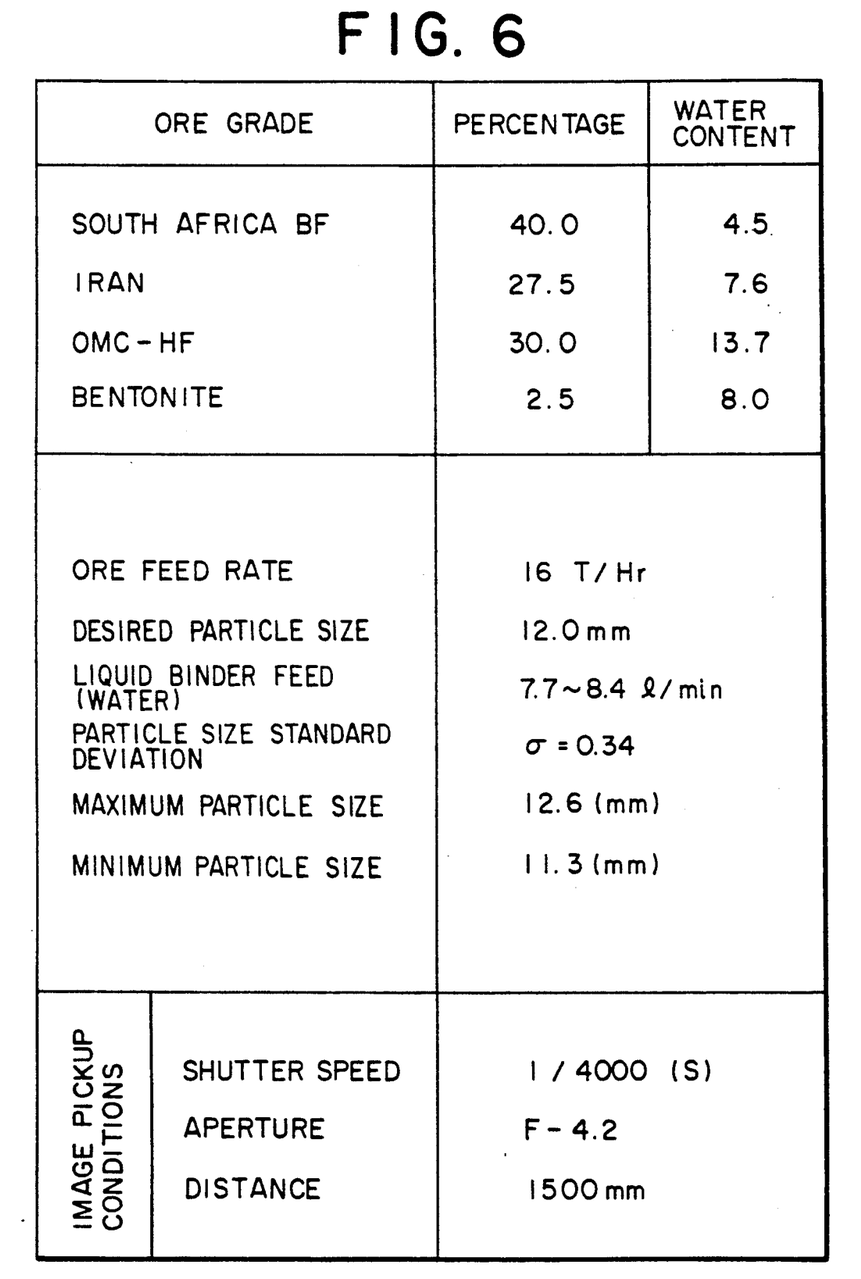
FIGS. 6 and 7 show respectively the manufacturing data of chromium ore pellets according to an automatic control and a manual control.
Figure 8:
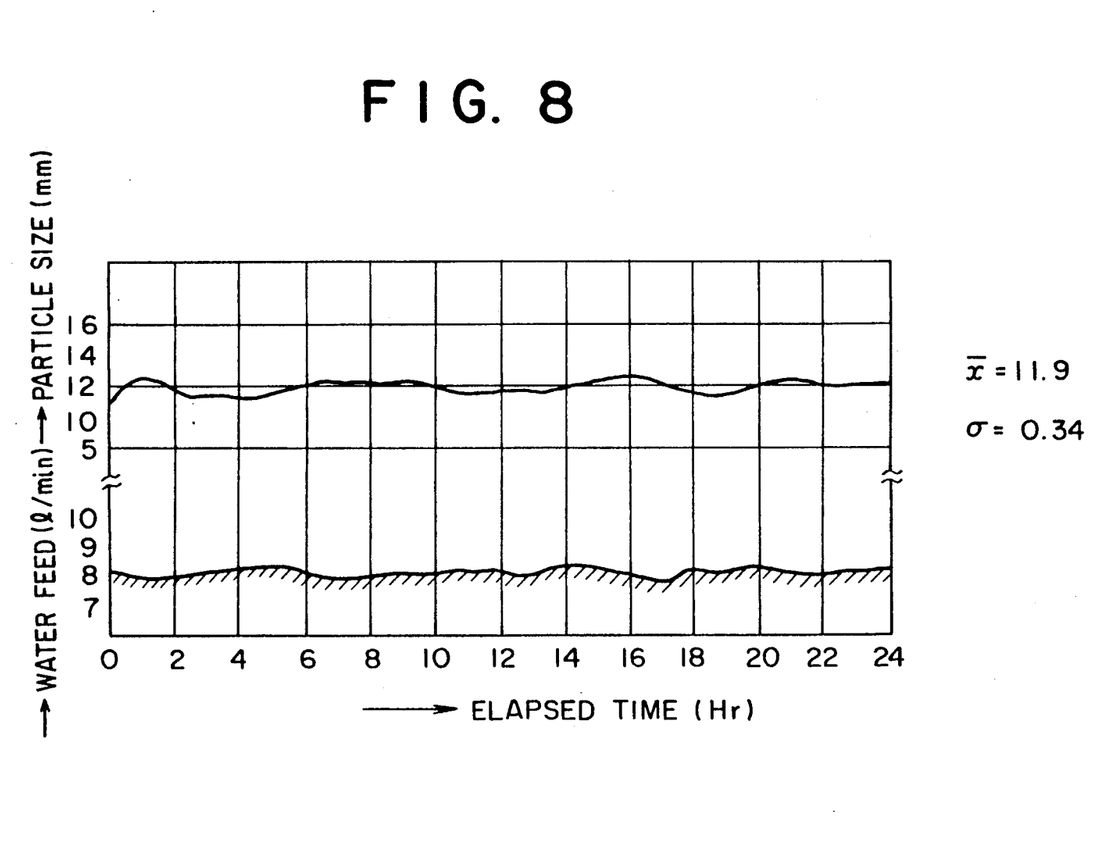
FIGS. 8 and 9 are characteristic diagram showing variations with time of the water feed and particle size according to the automatic control and the manual control, respectively.

FIG. 6 shows the manufacturing data of the chrominum ore pellets and FIG. 8 is a characteristic diagram showing the variations of the water feed and the particle size with time. It will be seen from the figures that, in accordance with the variations in the particle size, the water feed was continuously varied to correct the particle size. As a result, the particle size variations with respect to the desired particle size (12 mm) of the chromimum ore pellets were such that the standard deviation $\sigma = 0.34$, the maximum particle size = 12.6 mm and the minimum particle size = 11.3, showing the very small values.

COMPARATIVE EXAMPLE 1

The production of chronium ore pellets was effected by the manufacturing process shown in FIG. 5. 300 Tons of the same lot and the same chromium ore fines were subjected to the granulation process. However, the adjustment of the liquid binder (water) quantity was effected under manual control by the operator who judged visually the particle size of the pellets rolling in the rotary tray. The results are shown in FIGS. 7 and 9.

Figure 7:
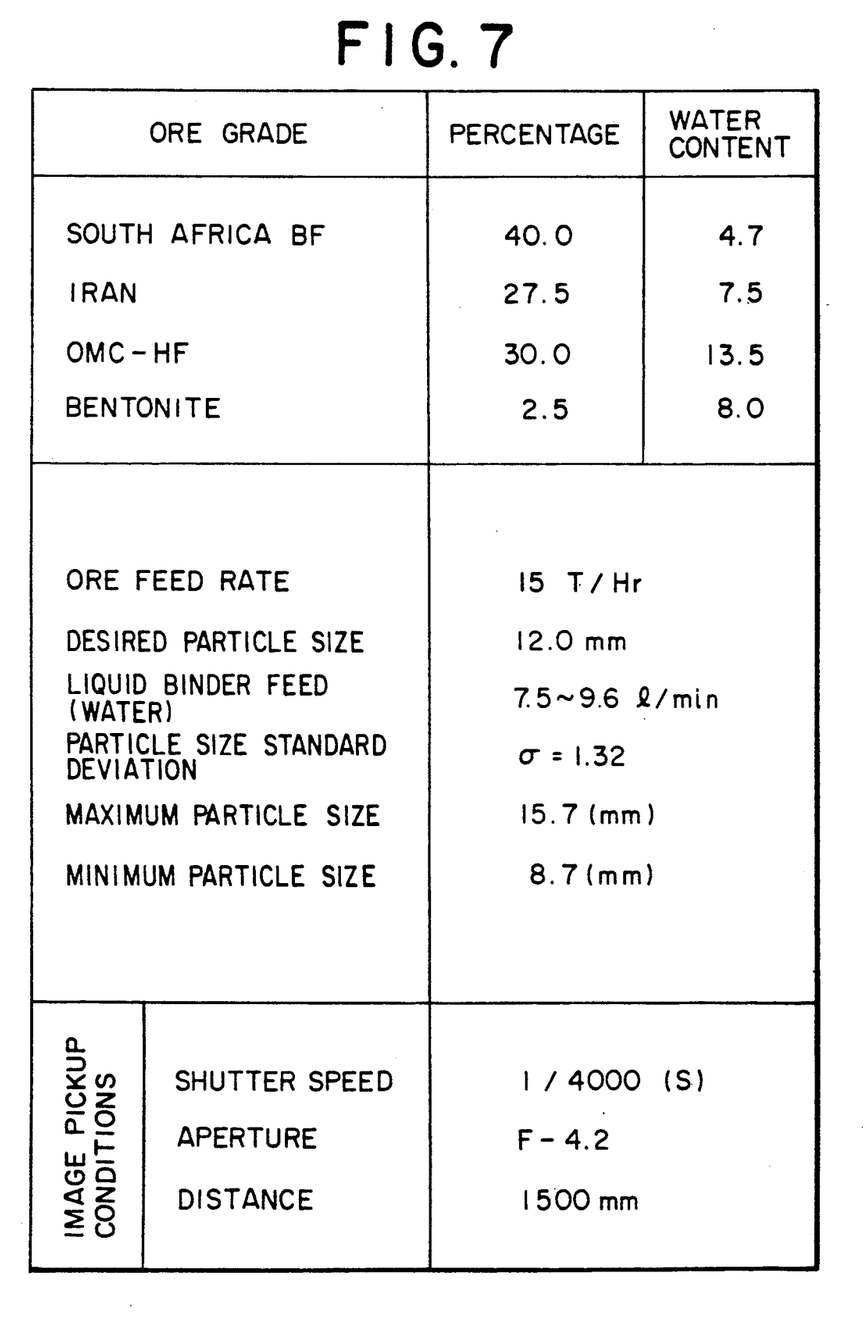
Figure 9:
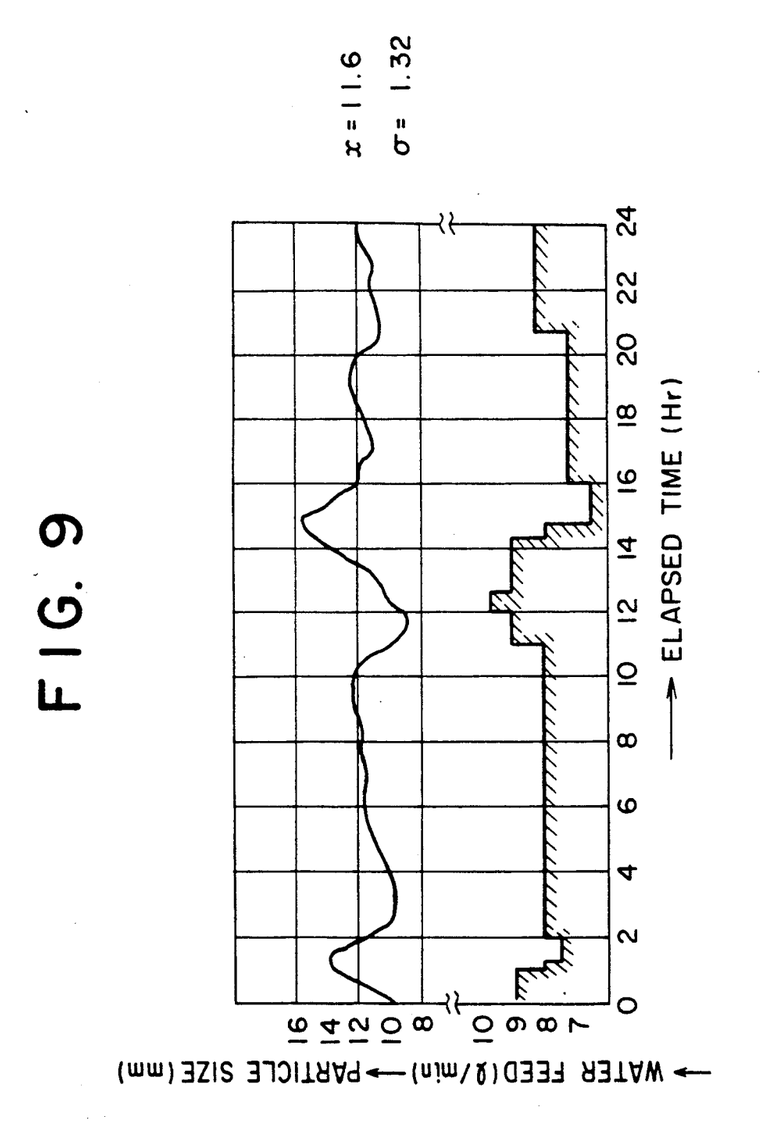

FIG. 7 shows the manufacturing data of the chromium ore, pellets and FIG. 9 is a characteristic diagram showing the variations of the water feed and the particle size with time. It will be seen from the figures that the particle size variations with respect to the desired particle size of the chromium ore pellets were such that the standard deviation $\sigma = 1.32$, the maximum particle size = 15.7 mm and the minimum particle size = 8.7 mm, showing the considerably large values as compared with Examples 1. Also, the load factor of the operator was about 1.5 times.

From the foregoing description it will be seen that due to the application of the granule average particle size measuring method according to the present invention to the rotary tray-type rolling granulation method of spraying a liquid binder onto the feed powder material in the rotary tray to form agglomerated granular material and utilizing the classifying effect of the rotary tray to discharge the granules grown to the desired particle size from a rim, the particle size of the granules in the rotary tray of the rotary tray-type rolling granulating machine can be continuously measured in real time so that the liquid binder quantity is adjusted to automatically control the particle size and the occurrence of any abnormal growth and defective growth of the particle size are prevented irrespective of variations in the various conditions, such as the moisture content and particulate properties, of the feed powder material which was not subjected to the preliminary treatments, thereby producing the uniform granules with a high degree of accuracy.

What is claimed is:

1. A method of measuring an average particle size of granules accumulated in a pile comprising the steps of:
   picking-up an image of granules accumulated in a pile,
   determining a moment of at least one order of an n-order moment $M_n$ ($n = 0, 1, 2, \ldots$) of spatial power spectrum of the picked-up image of said granules and determining the average particle size of the granules in accordance with said moment.

2. A method according to claim 1, wherein said n-order moment of a spatial power spectrum of said picked-up image is determined by horizontally dividing said image into $\underline{m}$ parts, averaging the image signal vertically in each of said divided parts to determine a spatial power spectrum of a resulting signal, averaging said determining $\underline{m}$ spatial power spectrum to obtain an average spatial spectrum P(u), and using said average spatial power spectrum P(U) to determine said n-order moment, $M_n$.

3. A method according to claim 1, wherein said n-order moment of a spatial power spectrum of said picked-up image is determined by vertically dividing said image into $\underline{m}$ parts, averaging the image signal horizontally in each of said divided parts to determine a spatial power spectrum of a resulting signal, averaging said determined $\underline{m}$ spatial power spectrum to obtain an average spatial power spectrum P(u), and using said average spatial power spectrum P(u) to determine said n-order moment, $M_n$.

4. A method according to claim 1, wherein use is made of an n-order moment $M_n$ ($n = 0, 1, 2, \ldots$) of a spatial power spectrum of a granule extracting image obtained by subjecting said picked-up image to binarization.

5. A method according to claim 1, wherein use is made of an n-order moment $M_n$ ($n = 0, 1, 2, \ldots$) of a spatial power spectrum of a granule extracting image obtained by subjecting said picked-up image to floating binarization.

6. A method according to claim 1, wherein two different order of moments $M_l$ and $M_{l+k}$ ($l = 0, 1, 2, \ldots$ $k = 1, 2, 3, \ldots$) in an n-order moment $M_n$ of a spatial power spectrum of said picked-up image are obtained, determining of an average particle size in accordance with said two moments of an order $M_l$ and $M_{l+k}$.

7. A method according to claim 6, wherein an average particle size $\bar{a}$ of granules is obtained from the following formulae:

$$\bar{a} = B \sqrt[k]{M_l / M_{l+k}} \qquad (B = \text{factor of proportionality})$$

8. A method according to claim 6, wherein use is made of spatial power spectrum of a granule extracting image obtained by subjecting said picked-up image to binarization.

9. A method according to claim 6, wherein use is made of spatial power spectrum of a granule extracting image obtained by subjecting said picked-up image to floating binarization.

10. According to claim 6, wherein two different order of moments $M_l$ and $M_{l+k}$ ($l = 0, 1, 2 \ldots, k = 1, 2, 3, \ldots$) are obtained by horizontally dividing said image into $\underline{m}$ parts averaging the image signal vertically in each of said divided parts to determine a spatial power spectrum of a resulting signal, averaging $\underline{m}$ power spectrum to obtain an average power spectrum P(u), and using said average spatial power spectrum P(u) to determine said moment $M_l$ and $M_{l+k}$.

11. According to claim 6, wherein two different order of moments $M_l$ and $M_{l+k}$ ($l = 0, 1, 2, \ldots, k = 1, 2, 3 \ldots$) are obtained by vertically dividing said image into $\underline{m}$ parts averaging the image signal horizontally in each of said divided parts to determine a spatial power spectrum of a resulting signal, averaging $\underline{m}$ power spectrum to obtain an average spatial power spectrum P(u), and using said average spatial power spectrum P(u) to determine said moment $M_l$ and $M_{l+k}$.

12. A method according to claim 6, wherein an average particle size of granules in a rotary tray of a rotary tray type rolling granulating machine is measured whereby a feed rate of a liquid binder is adjusted in accordance with a result of said measurement.

13. A method according to claim 1, wherein an average particle size of granules in a rotary tray of a rotary tray type rolling granulating machine is measured whereby a feed rate of a liquid binder is adjusted in accordance with a result of said measurement.

* * * * *